United States Patent [19]

Kuperus

[11] Patent Number: 4,581,221

[45] Date of Patent: Apr. 8, 1986

[54] ULCER DETECTION

[75] Inventor: John Kuperus, Long Beach, Calif.

[73] Assignee: Medi Nuclear Corporation, Inc., Baldwin Park, Calif.

[21] Appl. No.: 527,188

[22] Filed: Aug. 29, 1983

[51] Int. Cl.⁴ ..................... A61K 49/00; A61K 43/00
[52] U.S. Cl. .......................................... 424/1.1; 424/9
[58] Field of Search .................................... 424/1.1, 9

[56] References Cited

U.S. PATENT DOCUMENTS 3,852,413 12/1974 Cammarata .......................... 424/1.1
4,300,569 11/1981 Bonneau ............................... 424/1.1

OTHER PUBLICATIONS

Vasquez et al., Chemical Abstracts, 99 (1983) #49703q.

Primary Examiner—Christine M. Nucker
Attorney, Agent, or Firm—Bruce A. Jagger

[57] ABSTRACT

A carrier material is combined with Tc-99m and the resulting radiolabeled reagent is combined with a known ulcer-specific compound. The resultant agent, because of the ulcer-specific compound, tends to accumulate at the site of an ulcer in the digestive tract. The presence of localized concentrations of Tc-99m in the digestive tract indicates the existence and location of an ulcer. The Tc-99m is detected in the digestive tract by conventional radioimaging procedures.

9 Claims, No Drawings

ULCER DETECTION

This invention relates to ulcer detection and more particularly it relates to the use of technetium-labelled ulcer-specific compounds.

Previously, considerable difficulty had been experienced in diagnosing the existence of an ulcer in a digestive tract and in locating each of a plurality of ulcers in a digestive tract. Previous expedients for the diagnosis and location of ulcers included the use of radio-opaque materials such as barium, utilized with x-ray techniques, and various endoscopy procedures wherein a tube is inserted down the throat for the purpose of permitting viewing of a portion of the digestive tract. Barium occasionally causes bowel impaction, which in severe cases may require surgery to correct it. The diagnosis of ulcers often must be made under emergency conditions when there is doubt as to whether an ulcer or a heart attack is involved. Endoscopy procedures run the risk of precipitating or aggravating a heart attack. Both barium and endoscopy procedures are relatively expensive.

Various radio-labelled materials have been used in diagnostic procedures and one kind or another. Various ulcer-specific compounds are known which attach selectively to the site of an ulcer in the gastro-intestinal tract and do not attach to normal healthy walls of the gastrointestinal tract. The advantages of technetium 99 m for use in diagnostic procedures are known and include, for example, a short half-life of about six hours and the absence of primary Beta emission. Because of its short half-life, technetium is preferably combined with the material which it labels at or about the time of use. It is impractical to attempt to store technetium-labelled material. A chemical reaction to accomplish the labeling is usually carried out at the site of usage where only the routine conventional skill, knowledge and equipment which are common in small medical laboratories and offices are available. This generally limits the use of technetium to a few areas where labeling can be accomplished by simple easy-to-perform procedures.

According to the present invention, the advantages of technetium labeling are made available for use by ordinary clinical technicians in the routine diagnosis and location of ulcers in the gastrointestinal tract, despite the fact that the ulcer-specific compounds do not combine directly with technetium under the conditions which are required for use.

According to the present invention, a carrier material is allowed to react first at a predetermined pH with the technetium ion and the resulting reagent is then allowed to react at a second pH with an ulcer-specific compound. When ingested, the ulcer-specific compound attaches selectively through binding or precipitation to ulcerous tissue in the gastrointestinal tract. The unattached technetium-labelled material clears the stomach after a period of time, leaving the ulcer-specific compound present only at the ulcer sites. The quantity of labelled ulcer-specific compound is very small, so that clearing is accomplished as rapidly as possible and the ulcer sites are clearly defined. The ulcer sites are readily identifiable and locatable using conventional imaging procedures. The reactions which are performed at the sites of use are accomplished merely by the admixing of certain pre-prepared materials at room temperatures, using conventional procedures and equipment which are available in even the most minimally equipped locations. The reactions proceed safely to the desired end products without the necessity of any monitoring, so that nothing more than the minimal basic skills required of clinical technicians is needed. The cost of the ulcer-identification procedure according to the present invention is substantially less than the cost of either barium or endostopy procedures.

In carrying out the present invention according to a preferred embodiment, a suitable water-soluble carrier is admixed with a reducing agent and a water-soluble ulcer-specific compound. Generally the ulcer-specific compound and the carrier are not reacted at this time, thus leaving the reactive sites on the carrier available for attachment to the technetium ion. The preparation of this kit is generally performed at a manufacturing site where the necessary equipment and skilled personnel are available to accurately proportion the materials in the kit and to stabilize it for shipment and storage. The kit remains usable for long periods of time which may exceed one year. The kit is prepared so that only minimal handling and preparation are required at the site of use. At the site of use the clinical technician takes a fresh sample of technetium 99 m sodium pertechnetate and admixes it in an aqueous environment with the pre-prepared ulcer-specific compound-carrier-reducing agent and allows the resulting reaction to proceed. The pre-prepared materials in the kit and the instructions are such that the pH within the aqueous mixture will be within the range which is necessary to accomplish the reduction of the technetium compound and the reaction of the resulting technetium ion with the carrier to produce a labelled carrier. The pH is then adjusted either by the technician or, preferably, by ingestion into the digestive tract so as to permit the reaction between the labelled carrier and the ulcer-specific compound to proceed. Ingesting the admixture to accomplish the ulcer-specific compound-carrier reaction is preferred, because it avoids the necessity of adjusting the pH in vitro with the possible attendant errors.

In general, the kit containing the ulcer-specific compound, the carrier material and the reducing agent is prepared in an aqueous admixture which is then dehydrated, for example, by lypholyzation. The admixture may, however, be prepared, if desired, by admixing in carefully controlled proportions the ulcer-specific compound, the carrier material and the reducing agent as dry powders.

In order to stabilize the admixture and, in particular the reducing agent, the admixture is preferably prepared and stored in an inert environment such as under nitrogen. Dehydration is also preferred over storage in the liquid form, because the reducing agent and other materials are more stable in the dry form. The technician at the site of use, however, need not be concerned with maintaining an inert environment, because the reduction reaction and the other reactions will be carried to completion within a few minutes after the kit containing the ulcer-specific compound, carrier material and reducing agent is first opened.

The reactions by which the technetium compound is reduced to the technetium ion and the carrier material is reacted with that ion takes place at a pH of from about five to seven. If the admixture is allowed to become alkaline, the technetium ion is released from the carrier material. The reaction of the carrier technetium reagent with the ulcer-specific compound proceeds at a pH of from about two to four. Below this pH range, the ulcer-specific compound generally tends to precipitate out of solution so as to physically impede the progress of the reaction.

The materials and procedures are selected so that the carrier-technetium reaction proceeds first without any significant competition between the technetium and the ulcer-specific compound for reactive sites on the carrier. The technetium is present in very minute quantities as compared to the ulcer-specific compound. The carrier is present in much smaller quantities than the ulcer-specific compound. If the small amount of carrier were to be reacted first with the relatively greater amount of ulcer-specific compound, the subsequent reaction with the technetium ion would be hindered by the presence of the greater amount of ulcer-specific compound. This sequence of reactions is accomplished by taking advantage of the differing reactivities of these materials at different pH ranges.

In general the amount of technetium employed is from approximately one to two nanograms. This quantity is sufficient for imaging purposes and is small enough so that the amount of radiation is generally believed to be harmless. The carrier material is generally present in an amount of from approximately one to two milligrams and the ulcer-specific compound is generally present in an amount of from 20 to 100 milligrams. Although these are preferred quantities, the amount of technetium may range from approximately 0.4 to 10.0 nanograms, the amount of carrier may range from approximately 0.1 to 14.0 milligrams and the amount of ulcer-specific compound may range from approximately 10 to 200 milligrams. In general the quantity of ulcer-specific compound preferably should not exceed approximately 100 milligrams. That portion of the compound which does not attach to an ulcer tends to clear slowly from the stomach, thus, large excesses of this compound requires delays of as much as six to eight hours between the ingestion of the test material and the radioimaging. Such extended times between ingestion and imaging are inconvenient for the person being tested and, because of its short half-life, require that larger amounts of technetium be used.

Although a wide variety of carrier materials and ulcer-specific compounds can be utilized according to the present invention, it is preferred that lower molecular weight materials be used so as to increase their solubility at the pH levels which are encountered within the gastrointestinal tract. Using the preferred quantities of reagents and the preferred lower molecular weight materials, the ulcer-detecting agent which is not bound to the ulcer site clears from the stomach to such a degree that it is possible to perform radioimaging procedures within approximately one hour of the time the test material is ingested.

The ulcer-specific compounds are known and the choice of a particular compound, other than a preference for lower molecular weight materials, is not critical. Preferably, the ulcer-specific compound is chosen so that it is water soluble at the pH values involved, is compatible with the other materials and is not harmful. Suitable ulcer-specific compounds include, for example, the metal or basic salts of: maximally sulfated sucrose, lactose, maltose, raffinose, stachyose and the like. The suitable compounds include sulfated oligosaccharides, including starch-derived saccharides. The anticoagulant activity of these sulfate compounds tends to increase with increasing molecular weight. Anticoagulant activity is insignificant at the disaccharide level. Anticoagulant activity in an ulcer patient is generally undesirable. The degree of attachment to the ulcer site is generally dependent upon the extent of sulfation, with the degree of attachment increasing with the degree of sulfation. In general the sulphur content should be from approximately 10 to 22 weight percent and preferably from about 12 to 22 weight percent of the compound in the sodium salt. The clearance rate of the compound from the stomach is dependent on the molecular weight and salt form. In general, larger molecules tend to be more insoluble and to clear the normal tissue more slowly than smaller, more soluble molecules. Metal salts such as, for example, sodium, potassium, magnesium, calcium, barium and the like, tend to clear the normal tissue more rapidly than do basic salts such as, for example, aluminum hydroxide, magnesium hydroxide, and the like. The lower molecular weight maximally-sulfated metal salts are the preferred ulcer-specific compounds. Sodium sucrose octasulfate is a compound which exemplifies the preferred compounds. Mixtures of ulcer-specific compounds may be used, if desired.

Those carrier materials which are suitable for use according to the present invention comprise water-soluble molecules which contain at least one carboxyl group and at least one primary or secondary amine. A wide variety of materials are suitable for such use including, for example, amino acids, peptides, proteins and various chelating agents. The preferred carrier materials are those which contain two or more carboxyl groups and two or more amino or imino groups.

Preferably, the carrier materials are selected so that the reaction product of the carrier and ulcer-specific compound does not precipitate at pH values of from about 2 to 4. In general, very large molecular weight carrier materials tend to form reaction products which precipitate and delay clearance from normal gastrointestinal tissues. When large molecular weight carriers are combined with large molecular weight ulcer-specific compounds, the reaction product tends to precipitate. The carrier molecule should be selected so that it is compatible with the desired ulcer-specific compound and is not harmful. In general, the molecular weight of the carrier should be decreased as the molecular weight of the desired ulcer-specific compound increases.

It is believed that the labeling material binds to the carboxyl groups on the carrier and the amino or imino groups bind to the ulcer-specific compound. The efficiency of the labeling appears to increase as the number of carboxyl groups per molecule increases. The stability of the labelled carrier and ulcer-specific complex generally increases as the number of amino or imino groups per molecule increases. Human serum albumin is typical of the preferred carriers because it contains multiple attachment sites for both the labeling material and the sulfated saccharide. In general, proteins are the preferred carriers.

The quantities of carrier and ulcer-specific compound are proportioned so that great excesses of the carrier do not inactivate the ulcer-specific compound. In general, the molar ratio of carrier to ulcer-specific compound is from about 1:1 to 1:200 and preferably from about 1:5 to 1:150. For example, for the particularly preferred reagents, human serum albumin and sodium sucrose octasulfate, the molar ratio is from about 1:5 to 1:120 and is preferably approximately 1:100.

The technetium-labelled ulcer-specific compound in the intestinal tract at the site of an ulcer is believed to have the following general structural formula:

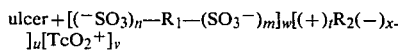

wherein $R_1$ is an oligosaccharide moiety; $R_2$ is selected from the group consisting of natural alpha amino acid moiety, natural di- and polypeptide moiety, natural protein moiety, diethyliminodiacetic acid moiety, paraisopropyliminodiacetic acid moiety, parabutyliminodiacetic acid moiety, diisopropyliminodiacetic acid moiety, iminodiacetic acid moiety, salts and mixtures thereof; n is an integer from about 1 to 6, preferably from about 3 to 6; m is an integer from about 1 to 6, preferably from about 3 to 6; w is an integer from about 1 to 9, preferably from about 3 to 9; u is an integer from about 1 to 8, preferably about 1, and u is less than w; v is an integer from about 1 to 12, preferably from about 2 to 12; t is an integer from about 1 to 9, preferably from about 3 to 9; and x is an integer from about 1 to 12, preferably from about 2 to 12. The pH in the stomach under extreme conditions ranges from approximately 1 to 4. This structural formula is believed to represent the compounds of this invention throughout the range of pH values found in the stomach.

The carrier compounds in aqueous admixtures at pH values of from about 1 to 7 have the general structural formula

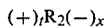

wherein $R_2$, t and x are as described hereinabove.

The ulcer-specific compounds in aqueous admixtures at pH values of from about 1 to 7 have the general structural formula

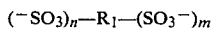

wherein $R_1$, n and m are as described hereinabove.

The following specific examples are submitted for the purposes of illustration only and not limitation. All parts and percentages are by weight unless otherwise indicated.

EXAMPLE I

A kit containing a protein carrier, a reducing agent and an ulcer-specific compound is prepared utilizing the following materials:

| | |
|---|---|
| $SnCl_2 2H_2O$ | 10 mg |
| Human serum albumin (HSA) 25% | 0.4 ml (100 mg. HSA) |
| 0.1 N HCl | 5 cc |
| Acetate buffer pH 5.5 1.2 N | 2 cc |
| Water for injection | 80 ml |
| Sodium lactose sulfate | 150 mg |
| Dry nitrogen gas apr. | |

The HSA is dissolved in the distilled water. The $SnCl_2 2H_2O$ is dissolved in the 0.1N HCl and added to the 0.4 ml HSA solution. The pH of the solution is adjusted to 5.5 with the acetate buffer, and the sodium lactose sulfate ulcer-specific compound is added. All solutions are purged with nitrogen to prevent oxidation of the stannous chloride. The final volume is then adjusted to 100 ml with distilled water and one ml volumes are dispensed into separate vials, lypholyzed, back-filled with dry nitrogen gas, and sealed. The resultant storable vials are ready for use.

The substitution of any one of the sodium or potassium salts of sucrose sulfate, maltose sulfate, raffinose sulfate or stachyose sulfate for the sodium lactose sulfate will result in a satisfactory product. In general, maximally sulfated disaccharide salts and water-soluble polysaccharide salts and mixtures thereof can be used for the ulcer-specific compound. Various other proteins, such as egg albumin, bovine albumin, fibrinogen, mixtures thereof or the like, when substituted for the HSA protein carrier give a satisfactory product. Because of the instability of the stannous ion, a large excess of stannous chloride is used which permits storage of the sealed vials for more than one year. Quantities of ulcer-specific compound of up to ten grams may be used, if desired. As much as 200 milligrams of the protein carrier may be used, if desired. Clearance times tend to increase with the use of increased quantities of materials.

The sealed vials are opened at the site of use and an aqueous Tc-99 m sodium pertechnetate solution containing about 2 nanograms of Tc-99 m ion is admixed with the contents of the vial and the volume of the admixture is adjusted to 10 ml with distilled water. The pH of the aqueous admixture is about 5.5 and the reaction between the Tc-99 m sodium pertechnetate and the stannous ion goes forward to reduce the pertechnetate compound to produce 99 m $TcO_2^+$ ion which in turn reacts with the protein carrier to produce a technetium labelled carrier reagent admixed with the ulcer-specific compound. This aqueous admixture is ingested and at the approximate pH 3 in the stomach the technetium labelled carrier reagent reacts with the ulcer-specific compound to label the ulcer-specific compound. The ulcer-specific compound binds with any ulcers which may be present. After the excess technetium labelled material clears the stomach in about one hour, radioimaging is carried out to diagnose and locate the ulcers. No special skill, knowledge or equipment beyond that usually found in small clinical laboratories is needed in using the kit in the detection of ulcers. Other natural proteins such as egg and bovine albumin and fibrinogen may be used in place of the human serum albumin with good results.

EXAMPLE II

A kit containing a chelating carrier, a reducing agent and an ulcer-specific compound is prepared utilizing the following materials:

| | |
|---|---|
| Sn metal | 60 mg |
| HCl 12 N | 2 cc |
| Diethyliminodiacetic acid (DIDA) | 5 gm |
| Acetate buffer pH 5.5 | 20 cc |
| Water | 1000 ml |
| Potassium sucrose sulfate | 20 gm |
| Dry nitrogen gas | |

The tin metal is dissolved in the concentrated hydrochloric acid. This is preferred over using a prepared stannous salt, as this avoids undesired stannous hydroxide formation which occurs spontaneously with storage of the salt. The presence of stannous hydroxide can lead to the formation of a Tc-99 m labelled colloid which would not label the sulfated ulcer-specific compound. The DIDA carrier is dissolved in 800 ml of water. When completely dissolved, the tin in 12N HCl is added to the DIDA solution. Nitrogen gas should be bubbling through the solution to expel oxygen from the solution and avoid stannous hydroxide formation. The pH is then adjusted to 5.5 using the acetate buffer. The potassium sucrose sulfate ulcer-specific compound is then added and dissolved. Water is added to reach 1,000 ml. One ml volumes are dispensed into 10 ml vials and lypholyzed under standard conditions. The vials are sealed under nitrogen for transportation, storage and in vivo use as described above in Example I. Other buffers such as phosphate buffer could be used, but acetate buffer is preferred, because the stannous ion does not form a complex with acetate buffer. When the stannous ion does form a complex with the buffer, the final result is often a technetium-labelled buffer which is ineffective for the intended purpose of ulcer detection.

Various metal salts of diethyliminodiacetic acid (DIDA) may also be used, if desired, in place of the DIDA. Other chelating agents such as paraisopropyliminodiacetic acid, parabutyliminodiacetic acid, diisopropyliminodiacetic acid, iminodiacetic acid, metal salts thereof, mixtures thereof, and the like may be used as the carrier with good results.

EXAMPLE III

In a preferred embodiment, a kit containing a protein carrier, a reducing agent and an ulcer-specific compound which is designed to form the final radio-labelled ulcer seeking agent in vivo is prepared utilizing the following materials:

| | |
|---|---|
| Tin metal | 6 mg |
| HCl 12 N | 1 cc |
| Human serum albumin | 100 mg |
| Acetate buffer 1.2 M pH 5.5 | 10 cc |
| Calcium sucrose octasulfate | 150 mg |
| Distilled water q.s. | 100 cc |
| Dry nitrogen gas q.s. | |

The tin metal is dissolved in the 12N HCl. The human serum albumin is dissolved in 80 cc of the distilled water. When the tin metal is totally dissolved in the 12N HCl, this tin solution is added slowly to the 80 cc of distilled water containing the human serum albumin, nitrogen gas should be bubbling through the solution to prevent oxidation of the stannous ion. The pH of the solution is adjusted to 5.5 with the acetate buffer and the sucrose sulfate ulcer-specific compound is added. The final volume is adjusted to 100 ml with distilled water and one ml volumes are dispensed into separate vials, lypholyzed, back-filled with dry nitrogen gas, and sealed. The resultant storable vials are ready for in vivo use as described above.

EXAMPLE IV

A kit for in vitro labeling of the ulcer-specific compound is prepared utilizing the following materials:

| Vial contents | |
|---|---|
| Stannous fluoride | 10 mg |
| HCl 0.1 N | 5 cc |
| Albumin, chicken egg | 100 mg |
| Sodium hydroxide 0.1 N | 6 cc |
| Water for injection | 80 ml |
| Potassium maltose sulfate | 200 mg |
| Dry nitrogen apr. | |

A simple solution, under nitrogen, of the stannous fluoride is prepared in the 0.1N HCl. The chicken egg albumin is dissolved in the 80 ml water for injection. The nitrogen gas is bubbled through the albumin solution while the stannous fluoride solution is added slowly, with stirring, to it. The pH of the solution is adjusted to 5.5–6.0 with the sodium hydroxide and the potassium maltose sulfate is added slowly. The final volume is adjusted to 100 cc with water for injection and one ml volumes are dispensed into separate vials, lypholyzed, back-filled with dry nitrogen gas, and sealed. The resultant storable vials are ready for use. Single use syringes are filled with 1.5 cc of the 0.1N HCl and one such syringe is packaged with each of the above described storable vials. In use, technetium 99 m sodium pertechnetate solution in a minimum volume of 3 cc is added to one of the above described storable vials which contains reducing agent, carrier and ulcer-specific compound. The mixture is allowed to react for five minutes to label the albumin after which the 1.5 cc HCl solution is added to the reaction vial from the syringe to reduce the pH to about 3. This causes the ulcer-specific compound to react with the technetium-99 m labeled albumin to form the radio labeled ulcer-specific compound. The labeled material is now ready for oral administration to the patient. The patient should be cautioned that this preparation may taste a little salty. Other carrier and ulcer-specific compounds may be substituted for the albumin and potassium maltose sulfate, as described herein, with satisfactory results.

EXAMPLE V

A kit for the in vitro labeling of an ulcer-specific compound which is in the basic salt form is prepared utilizing the following materials:

| Vial contents | |
|---|---|
| Stannous tartrate | 20 mg |
| HCl 0.1 N | 5 cc |
| Poly (Lys—HBr, Ala, Glu, Tyr)5:6:2:1 (acid salt of polyamino acid) | 20 mg |
| Potassium hydroxide 0.1 N | apr. |
| Water for injection | 80 cc |
| Sucrose polysulfate aluminum hydroxide | 1 gm |
| Dry nitrogen gas apr. | |

Under nitrogen a simple solution of stannous tartrate is prepared in the 0.1N HCl. The acid salt polyamino acid carrier is dissolved in the 80 cc of water for injection. Nitrogen gas is bubbled through this solution while the stannous tartrate solution is added to it with stirring. The pH of the solution is adjusted to 5.5–6.0 with 0.1N potassium hydroxide and the sucrose polysulfate aluminum hydroxide is added to it. The final volume is adjusted to 100 cc with water for injection and one ml volumes are dispensed into separate vials, lypholyzed, back-filled with dry nitrogen gas and sealed. The resultant storable vials are ready for use. Single-use syringes are each filled with 2 cc of 0.1N HCl and one such syringe is packaged with each of the above vials. In use technetium-99 m sodium pertechnetate solution in a volume of at least 2 cc is added to a vial containing the reducing agent, chelating carrier and basic salt ulcer-specific compound. The mixture is allowed to react for five minutes, so that the technetium becomes attached to the polyamino acid. The 2 cc of HCl is then added from the syringe to cause the ulcer-specific compound to attach to the polyamino acid which was radiolabeled in the previous reaction. This labeling proceeds rapidly at the reduced pH of about 3. The reaction product of the polyamino acid and the basic salt sulfated saccharide forms a sticky mass. This preparation is somewhat difficult for a person to take and increases the time required to carry out the test as compared with metallic salt materials. The mass acts as a solid in the stomach so that ulcers are often not labeled unless the mass comes in contact with the ulcer. Clearance of excess activity from the stomach is much delayed by reason of the physical characteristics of the labeled material.

EXAMPLE VI

A kit utilizing a basic salt compound is prepared utilizing the following materials:

| | |
|---|---|
| Stannous chloride | 10 mg |
| HCl 0.1 N | 5 cc |
| Bovine albumin | 100 mg |
| Acetate buffer pH 5.5 1 M | 80 ml |
| Distilled water | |
| Fructose polysulfate aluminum hydroxide | 0.5 g |
| Dry nitrogen gas apr. | |

A simple solution of stannous chloride is prepared under nitrogen in the 0.1N HCl. The bovine albumin carrier is dissolved in the distilled water and nitrogen gas is bubbled through the solution, while the stannous chloride solution is added slowly with constant stirring. The pH of this solution is then adjusted to 5.5 with the acetate buffer. The fructose polysulfate aluminum hydroxide ulcer-specific compound is added and the total volume is adjusted to 100 cc by the addition of distilled water. One ml volumes are dispensed into separate vials, lypholized, back-filled with nitrogen and sealed. The stable vials are ready for shipment and use. This kit is prepared for use by the addition of technetium Tc-99 m compound solution in a convenient volume, usually 5 cc. The carrier molecule is radiolabeled, but the ulcer-specific compound is not labeled with the radiolabeled carrier until after the mixture is administered orally to a patient and mixes with the acid pH of the stomach. The labeled product has the same solid sticky characteristics described above in Example V and has the same disadvantages of limited contact with ulcers and slow clearance of activity.

Various acid salts such as the HBr and HCl and acetate salts of amino acids, di- and polypeptides and proteins are useful as carriers in these examples.

What have been described are preferred embodiments in which changes and modifications may be made without departing from the spirit and scope of the accompanying claims.

What is claimed is:

1. Method comprising:

selecting a carrier compound having in aqueous admixtures at pH values of from about 7 to 1 the formula $$(+)_t R_2(-)_x$$

wherein $R_2$ is selected from the group consisting of natural alpha amino acid moiety, natural di- and polypeptide moiety, natural protein moiety, diethyliminodiacetic acid moiety, paraisopropyliminodiacetic acid moiety, parabutyliminodiacetic acid moiety, diisopropyliminodiacetic acid moiety, iminodiacetic acid moiety, salts andmixtures thereof; t is an integer from about 1 to 9; and x is an integer from about 1 to 12;

selecting a reducible Tc-99 m compound and a reducing agent for said tc-99 m compound;

selecting an ulcer binding agent having in aqueous admixtures at pH values of from about 7 to 1 the formula $$(^-SO_3)_n\text{—}R_1\text{—}(SO_3^-)_m$$

wherein $R_1$ is an oligosaccharide moiety; n is an integer of from about 1 to 6; and m is an integer of from about 1 to 6;

preparing an admixture of said ulcer binding agent said carrier compound and said reducing agent under an inert atmosphere in an aqueous medium at a pH of from about 5 to 7; and separating said admixture into dosage units.

2. A composition having in aqueous admixtures at pH values of less than about 4 the formula $$[(^-SO_3)_n\text{—}R_1\text{—}(SO_3^-)_m]_w[(+)_t R_2(-)_x]_u[TcO_2^+]_v$$

wherein $R_1$ is an oligosaccharide moiety; $R_2$ is selected from the group consisting of natural alpha amino acid moiety, natural di- and polypeptide moiety, natural protein moiety, diethyliminodiacetic acid moiety, paraisopropyliminodiacetic acid moiety, parabutyliminodiacetic acid moiety, diisopropyliminodiacetic acid moiety, iminodiacetic acid moiety, salts and mixtures thereof; n is an integer from about 1 to 6; m is an integer from about 1 to 6; w is an integer from about 1 to 9; u is an integer from about 1 to 8 and less than w; v is an integer from about 1 to 12; t is an integer from about 1 to 9; and x is an integer from about 1 to 12.

3. Method of producing an ulcer detecting agent comprising:

selecting an ulcer-specific compound;

selecting a carrier material;

creating an aqueous admixture including at least said carrier material and a Tc-99 m ion, said aqueous admixture having a pH of from about 5 to 7;

allowing said tc-99 m ion to combine with said carrier material to produce a reagent, adjusting the pH of said aqueous admixture to less than about 4 and allowing said ulcer-specific compound to combine with said reagent to produce an ulcer-detecting agent having the formula $$[(^-SO_3)_n\text{—}R_1\text{—}(SO_3^-)_m]_w[(+)_t R_2(-)_x]_u[TcO_2^+]_v$$

wherein $R_1$ is an oligosaccharide moiety; $R_2$ is selected from the group consisting of natural alpha amino acid moiety, natural di- and polypeptid moiety, natural protein moiety, diethyliminodiacetic and moiety, paraisopropyliminodiacetic acid moiety, parabutyliminodiacetic acid moiety, diisopropyliminodiacetic acid moiety, iminodiacetic acid moiety, salts and mixtures thereof; n is an integer from about 1 to 6; m is an integer from about 1 to 6; w is an integer from about 1 to 9; u is an integer from about 1 to 8 and less than w; v is an integer from about 1 to 12; t is an integer from about 1 to 9; and x is an integer from about 1 to 12.

4. Method of producing an ulcer detecting agent comprising:

selecting a proteinaceous carrier material, said carrier material being capable of combining with Tc-99 m ion and with a salt of a sulfated oligosaccharide ulcer-specific compound, said ulcer-specific compound being different from said carrier material;

creating an aqueous admixture including at least said carrier material and said Tc-99 mm ion, said aqueous admixture having a pH of from about 5 to 7;

allowing said Tc-99 mm ion to combine with said carrier material to produce a reagent, adjusting the pH of said aqueous admixture to less than about 4 and allowing said ulcer-specific compound to combine with said reagent to produce an ulcer detecting agent.

5. Method of producing an ulcer detecting agent comprising:

selecting a water-soluble proteinaceous carrier material, said carrier material being capable of combining with Tc-99 m ion and a salt of a sulfated oligosaccharide ulcer-specific compound;

admixing said carrier material with Tc-99 m ion in the presence of said ulcer-specific compound and allowing said carrier material to combine with said Tc-99 m ion to produce a carrier-Tc-99 m reagent, said reagent being non-ulcer-specific; and admixing said carrier-Tc-99 m reagent with a water-soluble ulcer-specific compound and allowing said carrier-Tc-99 m reagent to combine with said ulcer-specific compound to produce an ulcer detecting agent.

6. Method comprising:

selecting a non-ulcer-specific proteinaceous carrier compound, a reducible Tc-99 m compound, a reducing agent for said Tc-99 m compound, and a salt of a sulfated oligosaccharide ulcer binding agent;

preparing an admixture of said ulcer binding agent, said carrier compound and said reducing agent under an inert atmosphere in an aqueous medium at a pH of from about 5 to 7; and separating said admixture into dosage units.

7. Method comprising:

selecting a non-ulcer-specific proteinaceous carrier compound, a reducible Tc-99 m compound, a reducing agent for said Tc-99 m compound, and an ulcer binding agent;

preparing an admixture of said ulcer binding agent, said carrier compound and said reducing agent under an inert atmosphere in an aqueous medium at a pH of from about 5 to 7; and separating said admixture into dosage units.

8. Method of claim 5 including allowing said carrier-Tc-99 m reagent to combine in vivo with said ulcer-specific compound.

9. Method of claim 5 including allowing said carrier-Tc-99 m reagent to combine in vitro with said ulcer-specific compound.

* * * * *